United States Patent [19]

Najarian

[11] Patent Number: 5,662,934

[45] Date of Patent: Sep. 2, 1997

[54] COMPOSITIONS AND METHODS FOR LOWERING CHOLESTEROL WHILE MAINTAINING ANTIOXIDANT LEVELS

[76] Inventor: Thomas Najarian, 18 Mannix Cir., Belmont, Mass. 02178

[21] Appl. No.: 68,431

[22] Filed: May 27, 1993

Related U.S. Application Data

[63] Continuation-in-part of Ser. No. 890, Jan. 5, 1993, abandoned.

[51] Int. Cl.$^6$ .............................. A61K 9/14; A61K 9/20; A61K 9/48

[52] U.S. Cl. ........................ 424/464; 424/451; 424/489; 514/824

[58] Field of Search ........................... 514/824; 424/464, 424/441, 439, 451, 455, 489, 423

[56] References Cited

U.S. PATENT DOCUMENTS 5,278,189  1/1994  Rath et al. ............................. 514/561

FOREIGN PATENT DOCUMENTS

| | | | |
|---|---|---|---|
| 0 254 869 A2 | 2/1988 | European Pat. Off. | A61K 31/215 |
| 0 323 666 A1 | 7/1989 | European Pat. Off. | A61K 31/785 |
| 0 516 349 A2 | 12/1992 | European Pat. Off. | C07C 217/18 |

OTHER PUBLICATIONS

Harris, William S., Ph.D., "The Prevention of Atherosclerosis with Antioxidants", *Clin. Cardiol.*, (1992), vol. 15, pp. 636–640.

Kalyanaraman, B., et al., "Synergistic Interaction between the Probucol Phenoxyl Radical and Ascorbic Acid in Inhibiting the Oxidation of Low Density Lipoprotein", *The Journal of Biological Chemistry*, (1992), vol. 267, No. 10, pp. 6789–6795.

Fruchart, J.C., "LDL et Athérogenése: Nouveaux Concepts", *Sem Hop Paris*, (1989), vol. 65, No. 3, pp. 91–95.

Blickle, J.F., et al., "Le Traitement des Hypercholestérolémies: Aspects Récents", *J. Méd. Strasbourg*, (1990), vol. 21, No. 10 pp. 580–583.

Finckh, B., et al., "Antiatheroslerotic Effect of Probucol in WHHL Rabbits: Are there Plasma Parameters to Evaluate this Effect?", *Eur. J. Clin. Pharmacol.*, (1991), vol. 40 [Supp. 1], pp. S77–S80.

Manninen, Vesa, M.D., et al., "Lipid Alterations and Decline in the Incidence of Coronary Heart Disease in the Helsinki Heart Study", *Jama*, (1988), vol. 260, No. 5, pp. 641–651.

Fruchart, J.C., "Antioxidant Therapy and Uptake of Human Oxidized LDL by Macrophages", *Annals, New York Academy of Sciences*, (1989), vol. 570, pp. 447–448.

Albanes et al. "Serum beta–carotene before and after beta–carotene supplementation" European Journal of Clinical Nutrition 1992, vol. 46, pp. 15–24, received Mar. 28, 1991; accepted Jun. 27, 1991.

Chisolm G.M. "Antioxidants and Atherosclerosis: A Current Assessment" Clinical Cardiology 1991, vol. 14, pp. I-25-30.

The Lipid Research Clinics Investigators "The Lipid Research Clinics Coronary Primary Prevention Trail; Results of 6 years of Post–Trial Follow–up" Archives Internal Medicine Original Investigation 1992, vol. 152, pp. 1399–1410.

Heady et al. "WHO clofibrate/cholesterol trail: clarifications" The Lancet Letters to the Editor 1992,vol. 340, pp. 1405–1406.

Marenah et al. "Hypocholesterolaemia and non–cardiovascular disease: metabolic studies on subjects with low plasma cholesterol concentrations" British Medical Journal 1983, vol. 286, pp. 1603–1606.

Potischman et al. "Associations Between Breast Cancer, Plasma Triglycerides,and Cholesterol" Nutrition and Cancer 1991, vol. 15, pp. 205–215.

DeRijke et al. "Susceptibility of low–density lipoproteins to oxidation in coronary bypass patients" The Lancet 1992, vol. 340, Oct. 3.

Associated Press "Vitamin E Seems to Benefit Heart, 2 Studies Show" The New York Times National Thursday, Nov. 19, 1992.

Stahelin et al. "Plasma Antioxidant Vitamins and Subsequent Cancer Mortality in the 12–Year Follow–up of the Prospective Base Study" American Journal Epidemiology 1991, vol. 133, No. 8, pp. 766–775.

Strejan et al. "Suppression of Chronic–Relapsing Experimental Allergic Encephalomyelitis in Strain–13 Guinea Pigs by Administration of Liposome–Associated Myelin Basic Protein" Journal of Neuroimmunology 1984/85, vol. 7, pp. 27–41.

*Primary Examiner*—Thurman K. Pase
*Assistant Examiner*—James A. Spear
*Attorney, Agent, or Firm*—Lahive & Cockfield, LLP

[57] ABSTRACT

Compositions comprising a physiologically-acceptable antioxidant and a cholesterol-lowering agent for treating hypercholesterolemia and the accompanying lowering of antioxidant levels in an individual are disclosed. A preferred composition for use in reducing serum cholesterol levels while maintaining antioxidant levels in an individual comprises beta-carotene and gemfibrozil (LOPID®).

12 Claims, No Drawings

COMPOSITIONS AND METHODS FOR LOWERING CHOLESTEROL WHILE MAINTAINING ANTIOXIDANT LEVELS

RELATED APPLICATIONS

This application is a continuation-in-part of U.S. Ser. No. 08/000,890 filed on Jan. 5, 1993, now abandoned, the contents of which are incorporated herein by reference.

BACKGROUND OF THE INVENTION

It is widely acknowledged that high levels of cholesterol can lead to cardiovascular disease. In recent years, the need to maintain a healthy level of serum cholesterol has become increasingly important. However, many individuals find that this is only possible through the use of cholesterol-lowering agents. Several trials of the long-term effects of cholesterol-lowering drugs on patients have shown reduced death from and incidence of heart disease. (See Lipid Research Clinics Investigators, *Arch Intern Med* 152:1399–1410 (1992)). However, some long-term studies on cholesterol lowering have suggested that very low cholesterol levels in an individual may be associated with an increased risk of cancer death. (J. A. Heady, WHO Clofibrate/Cholesterol Trial: Clarifications, *The Lancet* 340:1405–1406 (1992); The Helsinki Heart Study, *JAMA* 260:641–665 (1988); and The Helsinki Heart Study 8.5 year cumulative update (1992)).

There is compelling evidence that oxidized low-density lipoprotein (LDL) plays an important role in the formation of artherosclerotic lesions. (Chisolm, *Clin. Cardiol.* 14:I-25 - I-30 (1991)). As LDL becomes oxidized, its properties and mechanisms of interaction with cells are altered extensively. These changes cause the oxidized LDL to act deleteriously at various levels of artherosclerotic lesion development. Recent studies have shown that taking antioxidants such as vitamin E or beta carotene, reduces an individual's risk of heart attack presumably by preventing the oxidation of LDL (See NY Times, p. A9, cols. 1–6, Nov. 19, 1992). In addition, studies have shown that individuals who have low plasma levels of antioxidants have an elevated risk of cancer. Stahelin et al., *Am J Epidemiology* 133:766–775 (1991); Potischman, et al., *Nutr. Cancer* 15:205–215 (1991).

SUMMARY OF THE INVENTION

The present invention is directed to compositions comprising a physiologically-acceptable antioxidant and a cholesterol-lowering agent for treating hypercholesterolemia and the accompanying lowering of antioxidant levels in an individual. Preferred compositions include beta-carotene and a cholesterol-lowering agent, such as gemfibrozil (LOPID®), for treating the aforementioned condition. Alternatively, a cholesterol-lowering agent can be administered in conjunction with a physiologically acceptable antioxidant e.g., simultaneously with or sequentially. Compositions of the invention are useful for administration to an individual to lower serum cholesterol levels while maintaining or elevating serum antioxidant levels in the individual.

DETAILED DESCRIPTION OF THE INVENTION

The present invention is directed to a composition and method which act to maintain proper levels of physiologically acceptable antioxidants in an individual while that individual is undergoing a cholesterol-lowering regimen. It was discovered that individuals who are treated with cholesterol-lowering agents often have reduced serum levels of biological antioxidants such as beta-carotene, vitamin A, vitamin E and vitamin C. Although the mechanism of this action is unclear, the lowering of antioxidants may be due to the fact that beta-carotene and vitamins A and E are fat- or lipid-soluble. Thus, as the individual's lipid levels decrease through use of a cholesterol-lowering agent, less lipid is available to solubilize the antioxidants and less antioxidant is available to the body. Individuals having reduced levels of serum antioxidants as a result of a cholesterol-lowering agent may have an increased risk of developing cancer. See e.g., Stahelin et al., *Am J Epidemiology.* 133:766–775 (1991).

Compositions within the scope of the invention comprise at least one physiologically acceptable antioxidant and a cholesterol-lowering agent. Such compositions can be administered to an individual to maintain antioxidant levels while reducing serum cholesterol levels. As noted, several vitamins may act as biological antioxidants including beta-carotene, vitamin A, vitamin C and vitamin E. These vitamins appear to work at different levels of carcinogenesis. Stahelin et al., *Am J Epidemiology* 133:766–775 (1991). Beta-carotene may act as a scavenger for free radicals in the body. Vitamin A (retinol) has been recognized as being able to interfere with carcinogenesis. See Goodman Gilman, *The Pharmacological Basis of Therapeutics*, Pergamon Press, New York (1990). It is likely that vitamin A acts at the promotion or progression phase of carcinogenesis. Vitamin C (ascorbic acid) may also act as an antioxidant by preventing nitrosamine formation in the stomach and reducing fecal mutagenicity. Vitamin E (alpha-tocopherol), when acting as an antioxidant, may inhibit the formation of carcinogenic promoters by protecting essential cellular constituents, such as the polyunsaturated fatty acids of cell membranes, from peroxidation and by preventing the formation of toxic oxidation products. These and other physiologically acceptable antioxidants are within the scope of the invention.

A number of agents are available for administration to an individual to lower the individual's concentration of plasma cholesterol. Currently, these agents fall into five categories: 3-hydroxy-3-methylglutaryl-coenzyme A (HMG CoA) reductase inhibitors; fibric acids; bile acid-binding resins; probucol; and niacin (nicotinic acid). Any one or a combination of cholesterol-lowering agents can be administered to an individual in conjunction with a physiologically acceptable antioxidant in the form of a therapeutic composition or separate compositions.

Cholesterol-lowering agents useful in methods and compositions of the invention include HMG CoA reductase inhibitors which are derived from certain species of fungus. Mevastatin, pravastatin (PRAVACHOL®), and lovastatin (MEVACOR®) are common examples of this type of drug. Mevastatin is derived from a species of *Penicillium* while lovastatin can be derived from a species of either *Aspergillus* or *Monascus*. Upon administration to an individual, these drugs typically produce a dose-related decrease in low-density lipoproteins (LDL)-cholesterol by blocking synthesis of cholesterol in the liver. These agents also result in an increase in the plasma concentration of high-density lipoprotein (HDL)-cholesterol in the individual and a decrease in triglyceride concentrations.

Other cholesterol-lowering agents within the scope of the invention include fibric acids which are members of a family of aryloxyisobutyric acids. Chief among these agents is gemfibrozil (LOPID®). Administration of gemfibrozil primarily results in lower concentrations of triglycerides and very low-density lipoprotein (VLDL)-cholesterol in an individual by increasing the activity of lipoprotein lipase. As a result, catabolism of VLDL, a triglyceride-rich lipoprotein is also increased. In addition, there is generally an accompanying rise in the concentration of HDL in plasma of the individual. However, gemfibrozil is less effective in lowering the plasma concentration of LDL. Other aspects of the mechanism of action of fibric acids remains unclear.

Bile acid-binding resins are another family of cholesterol-lowering agents useful in compositions and methods of the present invention. The most commonly used agent in this family is cholestyramine (CHOLYBAR®, QUESTRAN®), the chloride salt of a basic anion-exchange resin. Cholestyramine lowers the concentration of plasma LDL but has little predictable effect on the level of HDL in plasma. Administered orally, cholestyramine is not absorbed by the body and binds bile acids in the intestine. As the bile acids are removed, conversion of cholesterol to bile acids increases. In response to this, the number of hepatic LDL receptors rises leading to an increased uptake of LDL from plasma. Thus, the level of plasma LDL-cholesterol decreases. The effectiveness of this family of agents and that of the HMG CoA reductase inhibitors are markedly increased when these two agents are used together.

Another cholesterol-lowering agent within the scope of the invention is probucol (LORELCO®), a synthetic lipophilic antioxidant related structurally to butylated hydroxytoluene. Probucol is not structurally related to any other available cholesterol-lowering agent. Although probucol minimally reduces LDL-cholesterol, it's primary effect is a reduction in HDL- cholesterol. Probucol also has a minimal effect on the concentrations of triglycerides and VLDL. The mechanism of action of probucol is not known.

Niacin (nicotinic acid) is another agent which may be used in compositions of the invention to lower the concentration of plasma cholesterol. Upon administration, niacin lowers triglycerides, VLDL, and LDL-cholesterol with an accompanying increase in the concentration of HDL-cholesterol. When administered in combination with a bile acid-binding resin, there is a further significant reduction in LDL-cholesterol. The mechanism by which niacin reduces lipid concentrations is unclear. Niacin does next appear to alter the total body synthesis of cholesterol nor does it alter the excretion of bile acids. The lipid-lowering property of niacin is not shared by nicotinamide and has nothing to do with the role of niacin as a vitamin.

Therapeutic compositions and combinations of a physiologically acceptable antioxidant and a cholesterol-lowering agent can be administered to an individual to reduce serum cholesterol levels while maintaining antioxidant levels in the individual. A physiologically acceptable antioxidant and a cholesterol-lowering agent can be administered in the form of a therapeutic composition in an amount effective to maintain or increase serum antioxidant levels while reducing serum cholesterol levels. Alternatively, a physiologically acceptable antioxidant and a cholesterol-lowering agent can be co-administered, simultaneously or sequentially. Administration of such compositions or combinations of the present invention to an individual can be carried out using known procedures, at dosages and for periods of time effective to reduce the concentration of plasma cholesterol and to maintain the level of antioxidants in the individual's serum. In addition, such compositions or combinations may be administered to an individual already receiving a cholesterol lowering regimen to restore or increase biological antioxidant levels in the individual.

Effective amounts oft he compositions or combinations of the invention will vary according to factors such as the age, sex, and weight of the individual. Dosage regima may be adjusted to provide the optimum therapeutic response. For example, in the case of LOPID®, the optimal therapeutic dose to be administered to an individual should be about 600 mg twice a day of LOPID® with 5000–15,000 units of an antioxidant, such as beta-carotene twice a day. However, the range of effective doses for LOPID® should be from about 100 mg daily to about 2000 mg daily. The optimal dosages for other cholesterol-lowering agents are determined by reference to the usual dose and manner of administration of such cholesterol-lowering agent. For example, the range of effective dosages for other agents is as follows: niacin, from about 500 mg to about 4000 mg/day; MEVOCOR®, from about 20 mg to about 80 mg/day; and PRAVOCHOL®, from about 10 mg to about 40 mg/day. The dosage range of beta-carotene should be from about 1000 units to about 100,000 units daily. The dosage range for other physiologically acceptable antioxidants is determined by reference to the usual dose and manner of administration of the antioxidant. For example, a range of from about 100 units to about 4000 units/day of vitamin E; from about 100 mg to about 5000 mg/day of vitamin C; and from about 1000 units to about 25,000 units/day of vitamin A. The composition or combination of agents should be administered in amounts sufficient to ensure that the serum level of antioxidants is maintained at an appropriate level or restored or increased to an appropriate level while serum cholesterol levels are reduced.

The method of administration of compositions or combinations of the invention will depend on the type of cholesterol-lowering agent used and the antioxidant chosen. The cholesterol-lowering agent and the antioxidant may be administered together in the same composition or simultaneously or sequentially in two separate compositions. Also, one or more physiologically acceptable antioxidants or one or more cholesterol-lowering agents may be administered to an individual either in the form of a therapeutic composition or in combination, e.g., in the form of one or more separate compositions administered simultaneously or sequentially. The sequence of administration will be dependent on the type of antioxidant(s) and cholesterol-lowering agent(s) chosen. For example, in the case of a bile acid-binding resin administered orally, the antioxidant would be administered prior to administration of the bile acid-binding resin to prevent interference with proper absorption of the antioxidant.

A physiologically acceptable antioxidant alone, or in combination with a cholesterol-lowering agent in the form of a composition, can be administered in a convenient manner such as by injection (subcutaneous, intravenous, etc.), oral administration, inhalation, transdermal application, or rectal administration. Depending on the route of administration, the composition containing the antioxidant and cholesterol-lowering agent may be coated with a material to protect the compound from the action of acids and other natural conditions which may inactivate the antioxidant.

To administer the composition by other than parenteral administration, it may be necessary to coat the composition with, or co-administer the composition with, a material to prevent its inactivation. For example, the composition may be administered to an individual in an appropriate diluent or in an appropriate carrier such as liposomes. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The composition containing the antioxidant and cholesterol-lowering agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition containing the antioxidant in the required amount in an appropriate solvent with one or a combination of ingredients enumerated above, as required. Generally, dispersions are prepared by incorporating the composition into a sterile vehicle which contains a basic dispersion medium and the required other ingredients from those enumerated above.

When the composition containing the antioxidant is suitably protected, as described above, the composition may be orally administered, for example, with an inert diluent or an assimilable edible carrier. The composition and other ingredients may also be enclosed in a hard or soft shell gelatin capsule, compressed into tablets, or incorporated directly into the individual's diet. For oral therapeutic administration, the composition may be incorporated with excipients and used in the form of ingestible tablets, buccal tablets, troches, capsules, elixirs, suspensions, syrups, wafers, and the like. The percentage of the compositions and preparations may, of course, be varied. The amount of active compound in such therapeutically useful compositions is such that a suitable dosage will be obtained.

The tablets, troches, pills, capsules and the like may also contain a binder, an excipient, a lubricant, or a sweetening agent. Various other materials may be present as coatings or to otherwise modify the physical form of the dosage unit. For instance, tablets, pills, or capsules may be coated with shellac, sugar or both. Of course, any material used in preparing any dosage unit form should be pharmaceutically pure and substantially non-toxic in the amounts employed.

As used herein "pharmaceutically acceptable carrier" includes any solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in compositions of the invention is contemplated.

It is especially advantageous to formulate compositions of the invention in dosage unit form for ease of administration and uniformity of dosage. Dosage unit form as used herein refers to physically discrete units suited as unitary dosages for the individuals to be treated. Each dosage contains a predetermined quantity of active compound calculated to produce the desired therapeutic effect in association with the required pharmaceutical carrier. The specification for the novel dosage unit forms of the invention is dependent on the unique characteristics of the composition containing the antioxidant and the particular therapeutic effect to be achieved. Dosages are determined by reference to the usual dose and manner of administration of the ingredients.

This invention is further illustrated by the following, non-limiting exemplification.

EXEMPLIFICATION

The effect of each of the cholesterol-lowering drugs LOPID® (gemfibrozil), PREVACHOL® (prevastatin), and QUESTRAN® (cholestryramine) on serum beta-carotene levels was determined. Twelve individuals were chosen at random and enrolled in the program on various dates. Each individual had a cholesterol level of over 175 mg/dl and a cholesterol/HDL ratio of 4.8 or higher. None of the individuals took vitamin supplements or cholesterol-lowering agents prior to this study. All samples were analyzed by METAPATH® New England (63–65 Rogers Street, Cambridge, Mass.).

A fasting blood sample was taken from each individual prior to beginning a cholesterol-lowering regimen. Nine of the twelve individuals were placed on LOPID®, two on PREVACHOL®, and one on QUESTRAN®. Other than instructing the individuals to avoid fatty foods, no change was advised in their diets. They were also told not to start taking vitamins of any kind. A fasting blood sample was taken from each of the individuals after a period of time on the cholesterol-lowering drug ranging from 54 to 139 days.

After the initial period of administration of the cholesterol-lowering drug alone, the individuals were then instructed to take beta-carotene supplements of 25,000 or 50,000 units daily in conjunction with the drug. A fasting blood sample was again taken from each individual after a period of time ranging from four to 28 days on this regimen.

The nine individuals placed on a LOPID® regimen were instructed to take 600 mg of LOPID® twice a day, one-half hour before meals. After a period of time, the individuals were instructed to take 25,000 units of beta-carotene in conjunction with LOPID®. The results of the LOPID®/Beta-Carotene study are shown in Table I. Five (AM, DS, JC, SZ, and LB) of the nine patients responded to the LOPID® treatment, demonstrating a decrease in cholesterol levels. As expected, these five patients also demonstrated a decrease in serum beta-carotene levels when taking LOPID® alone. However, serum beta-carotene levels were restored following a regime where beta-carotene was taken in conjunction with LOPID®. The cholesterol levels of these patients remained below their initial cholesterol levels during treatment with beta-carotene in conjunction with LOPID®.

As one illustrative example, a fasting blood sample was taken from patient JC after 92 days of treatment with LOPID®. During that time, this patient's cholesterol level decreased from an initial level of 268 mg/dl to 243 mg/dl, as shown in Table I. Meanwhile, this individual's initial data and results show a decrease in his serum beta-carotene level from 162.0 µg/dl to 91.5 µg/dl. Twenty-one days of subsequent treatment with LOPID® plus beta-carotene resulted in an increase in serum beta-carotene levels from 91.5 µg/dl to 101.7 µg/dl. Meanwhile, this patient's cholesterol level continued to decrease from 243 mg/dl to 231 mg/dl.

Two of the nine patients (PJ and RZ) demonstrated an increase in serum beta-carotene levels when taking LOPID® alone. This increase continued when beta-carotene was taken in conjunction with LOPID®. Another patient, patient FV, although instructed to take 600 mg of LOPID® twice a day, failed to do so during the first two months of treatment. During this time, this patient's serum beta-carotene level increased. After treatment with LOPID® together with beta-carotene, this patient's serum beta-carotene level remained essentially the same. Finally, patient SH showed a decrease in his serum beta-carotene level while on LOPID® but due to poor response to that drug with regard to his serum cholesterol level, this patient's treatment was changed to PROVACHOL®.

Similar results were obtained when this regimen was repeated with two patients BF and JS, with the exception that PROVACHOL® replaced LOPID® as the cholesterol-lowering agent. The results of this study are shown in Table II. Patients BF and JS were instructed to take 20 mg/dl of PROVACHOL® daily for a period of time, after which they were then instructed to take 50,000 units of beta-carotene in conjunction with PROVACHOL®. As shown in Table II, treatment with PROVACHOL® alone over 54 days resulted in a decrease in patient BF's initial cholesterol level from 202 mg/dl to 135 mg/dl, and a decrease in the initial serum beta-carotene level from 87.1 µg/dl to 56.6 µg/dl. When this patient was treated with beta-carotene in conjunction with PROVACHOL®, his serum beta-carotene level increased from 56.6 µg/dl to 126.7 µg/dl after 20 days, with his cholesterol level remaining essentially the same at 132 mg/dl. Likewise, as shown in Table II, after 56 days on PROVACHOL® alone, patient JS's cholesterol level decreased from 176 mg/dl to 124 mg/dl while his serum beta-carotene level decreased from an initial level of 42.9 µg/dl to 34 µg/dl. When treated with beta-carotene in conjunction with PROVACHOL® over 31 days, patient JS's cholesterol level remained steady at 123 mg/dl while his serum beta-carotene level increased to 77.1 µg/dl.

The regimen was again repeated with similar results when QUESTRAN® was administered as the cholesterol-lowering agent. The results of this study with one patient are shown in Table III. Patient PC was instructed to take two packages of QUESTRAN® daily for a period of time, after which she was instructed to take 50,000 units of beta-carotene in conjunction with the QUESTRAN®. As shown in Table III, patient PC's cholesterol level decreased from 325 mg/dl to 300.5 mg/dl while her serum beta-carotene level decreased from an initial level of 106.6 µg/dl to 46.5 µg/dl after 30 days of treatment with QUESTRAN® alone. Following 27 days of treatment with beta-carotene in conjunction with QUESTRAN®, this patient's cholesterol level continued to decrease from 300.5 mg/dl to 267 mg/dl while her serum beta-carotene level increased from 46.5 µg/dl to 150 µg/dl.

Responsiveness with regard to serum-cholesterol levels to each cholesterol-lowering agent varied from individual to individual. However, the above exemplification demonstrates that treatment with beta-carotene in conjunction with a cholesterol-lowering agent can restore serum beta-carotene levels in an individual taking a cholesterol-lowering agent, thus maintaining proper levels of antioxidants in individuals undergoing cholesterol-lowering regimens.

Although the invention has been described with reference to the preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

TABLE 1

LOPID® -AND BETA-CAROTINE STUDY

| | | | Basement Levels | | | | | Lopid® Only | | | | | |
|---|---|---|---|---|---|---|---|---|---|---|---|---|---|
| PATIENT # | AGE | SEX | Chol mg/dl | Trig mg/dl | HDL mg/dl | Chol/HDL Ratio | Beta-Carotene µg/dl | Duration (Days) | Chol mg/dl | Trig mg/dl | HDL mg/dl | Chol/HDL Ratio | Beta-Carotene µg/dl | % Decline in Beta-Carotene |
| 1 (AM) | 45 | M | 288 | 167 | 34 | 8.47 | 135.1 | 54 | 274 | 101 | 45 | 6.09 | 106.4 | 21% |
| | | | | | | | | 82 | 240 | 121 | 37 | 6.49 | 89.9 | 33% |
| 2 (FV)* | 50 | M | 223 | 96 | 40 | 5.58 | 83.5 | 70 | 253 | 155 | 42 | 6.02 | 104 | (25%) |
| 3 (SH) | 29 | M | 237 | 200 | 41 | 5.74 | 160 | 93 | 289 | 174 | 36 | 8.03 | 99.7 | 38% |
| 4 (DS) | 27 | M | 211 | 265 | 43 | 4.91 | 62.3 | 92 | 156 | 104 | 37 | 4.22 | 53.5 | 14% |
| 5 (JC) | 44 | M | 268 | 110 | 43 | 6.23 | 162.0 | 92 | 243 | 89 | 45 | 5.40 | 91.5 | 44% |
| 6 (SZ) | 44 | M | 221 | 333 | 20 | 11.05 | 122.2 | 85 | 194 | 150 | 40 | 4.85 | 54 | 56% |
| 7 (LB) | 60 | M | 232 | 208 | 43 | 5.40 | 156.3 | 97 | 224 | 96 | 54 | 4.15 | 116.1 | 26% |
| 8 (PJ) | 64 | M | 217 | 178 | 33 | 6.58 | 67.4 | 139 | 232 | 142 | 34 | 6.82 | 90.2 | (34%) |
| 9 (RZ) | 63 | M | 219 | 436 | 30 | 7.30 | 68.1 | 111 | 229 | 437 | 24 | 9.54 | 98.4 | (44%) |

TABLE 1-continued

LOPID® -AND BETA-CAROTINE STUDY

| | | | Lopid® + Beta-Carotene | | | | | |
|---|---|---|---|---|---|---|---|---|
| PATIENT # | AGE | SEX | Duration (Days) | Chol mg/dl | Trig mg/dl | HDL mg/dl | Chol/HDL Ratio | Beta-Carotene µg/dl |
| 1 (AM) | 45 | M | 4 | 268 | 198 | 40 | 6.70 | 105.1 |
| 2 (FV)* | 50 | M | 14 | 234 | 72 | 40 | 5.95 | 102.1 |
| 3 (SH) | 29 | M | change to PROVACHOL® because of poor response to LOPID® | | | | | |
| 4 (DS) | 27 | M | 28 | 170 | 136 | 34 | 5.00 | 138.8 |
| 5 (JC) | 44 | M | 21 | 231 | 90 | 42 | 5.50 | 101.7 |
| 6 (SZ) | 44 | M | 28 | 209 | 147 | 43 | 4.86 | 155.0 |
| 7 (LB) | 60 | M | 23 | 225 | 105 | 51 | 4.41 | 210.5 |
| 8 (PJ) | 64 | M | 21 | 225 | 116 | 38 | 5.92 | 120.9 |
| 9 (RZ) | 63 | M | 28 | 204 | 564 | 24 | 8.50 | 108.9 |

*Patient admitted to not taking LOPID® until second visit.

TABLE 2

PROVACHOL® AND BETA-CAROTENE STUDY

| | | | Basement Levels | | | | | Provachol® Only | | | | | | % |
|---|---|---|---|---|---|---|---|---|---|---|---|---|---|---|
| PATIENT # | AGE | SEX | Chol mg/dl | Trig mg/dl | HDL mg/dl | Chol/HDL Ratio | Beta-Carotene µg/dl | Duration (Days) | Chol mg/dl | Trig mg/dl | HDL mg/dl | Chol/HDL Ratio | Beta-Carotene µg/dl | Decline in Beta-Carotene |
| 1 (BF) | 67 | M | 202 | 317 | 32 | 6.31 | 87.1 | 54 | 135 | 135 | 28 | 4.82 | 56.6 | 35% |
| 2 (JS) | 63 | M | 176 | 91 | 27 | 6.52 | 42.9 | 56 | 124 | 105 | 24 | 5.17 | 34 | 21% |

| | | | Provachol® + Beta-Carotene | | | | | |
|---|---|---|---|---|---|---|---|---|
| PATIENT # | AGE | SEX | Duration (Days) | Chol mg/dl | Trig mg/dl | HDL mg/dl | Chol/HDL Ratio | Beta-Carotene µg/dl |
| 1 (BF) | 67 | M | 20 | 132 | 167 | 27 | 4.89 | 126.7 |
| 2 (JS) | 63 | M | 31 | 123 | 86 | 28 | 4.39 | 77.1 |

TABLE 3

QUESTRAN® -AND BETA-CAROTENE STUDY

| | | | Basement Levels | | | | | Questran® Only | | | | | | % |
|---|---|---|---|---|---|---|---|---|---|---|---|---|---|---|
| PATIENT # | AGE | SEX | Chol mg/dl | Trig mg/dl | HDL mg/dl | Chol/HDL Ratio | Beta-Carotene µg/dl | Duration (Days) | Chol mg/dl | Trig mg/dl | HDL mg/dl | Chol/HDL Ratio | Beta-Carotene µg/dl | Decline in Beta-Carotene |
| 1 (PC) | 63 | F | 325 | 285 | 51 | 6.37 | 106.6 | 30 | 300.5 | 277.7 | 52.3 | 5.7 | 46.5 | 56% |

| | | | Questran® + Beta-Carotene | | | | | |
|---|---|---|---|---|---|---|---|---|
| PATIENT # | AGE | SEX | Duration (Days) | Chol mg/dl | Trig mg/dl | HDL mg/dl | Chol/HDL Ratio | Beta-Carotene µg/dl |
| 1 (PC) | 63 | F | 27 | 267 | 249 | 48 | 5.6 | 150.8 |

I claim:

1. A method of lowering serum cholesterol levels in an individual comprising administering to the individual beta-carotene in conjunction with gemfibrozil, in an amount effective to maintain serum antioxidant levels and reduce serum cholesterol levels in the individual.

2. A method of claim 1 further comprising administering an antioxidant selected from the group consisting of ascorbic acid, alpha-tocopherol, and retinol.

3. A method of lowering serum cholesterol levels in an individual comprising administering to the individual a composition consisting essentially of beta-carotene and gemfibrozil, in an amount effective to maintain serum antioxidant levels and reduce serum cholesterol levels in the individual.

4. A composition consisting essentially of an effective serum cholesterol lowering amount of beta-carotene, a 3-hydroxy-3-methylglutaryl-coenzyme A reductase inhibitor, and an antioxidant selected from the group consisting of ascorbic acid, alpha-tocopherol and retinol such that serum antioxidant levels in an individual are elevated or maintained upon administration of the composition to the individual.

5. A composition consisting essentially of an effective serum cholesterol lowering mount of beta-carotene, niacin and an antioxidant selected from the group consisting of ascorbic acid, alpha-tocopherol and retinol such that serum antioxidant levels in an individual are elevated or maintained upon administration of the composition to the individual.

6. A composition consisting essentially of an effective serum cholesterol lowering amount of beta-carotene, a bile acid-binding resin and an antioxidant selected from the group consisting of ascorbic acid, alpha-tocopherol and retinol such that serum antioxidant levels in an individual are elevated or maintained upon administration of the composition to the individual.

7. A composition consisting essentially or an effective serum cholesterol lowering mount of beta-carotene and a fibric acid and an antioxidant selected from the group consisting of aseorbic acid, alpha-tocopherol and retinol such that serum antioxidant levels in an individual are elevated or maintained upon administration of the composition to the individual.

8. A method of lowering serum cholesterol levels in an individual comprising administering to the individual a composition consisting essentially of beta-carotene and a 3-hydroxy-3-methylglutaryl-coenzyme A reductase inhibitor in an amount effective to maintain serum antioxidant levels and reduce serum cholesterol levels in the individual.

9. A method of lowering serum cholesterol levels in an individual comprising administering to the individual a composition consisting essentially of beta-carotene and niacin in an amount effective to maintain serum antioxidant levels and reduce serum cholesterol levels in the individual.

10. A method of lowering serum cholesterol levels in an individual comprising administering to the individual a composition consisting essentially of beta-carotene and a bile acid-binding resin in an amount effective to maintain serum antioxidant levels and reduce serum cholesterol levels in the individual.

11. A method of lowering serum cholesterol levels in an individual comprising administering to the individual a composition consisting essentially of beta-carotene and a fibric acid in an amount effective to maintain serum antioxidant levels and reduce serum cholesterol levels in the individual.

12. A method according to any of claims 5–11, wherein the method comprises the further step of administering to the individual an antioxidant selected from the group consisting of ascorbic acid, alpha-tocopherol, and retinol.

* * * * *